(12) United States Patent
Li et al.

(10) Patent No.: US 11,435,330 B2
(45) Date of Patent: Sep. 6, 2022

(54) MITIGATION OF FRICTION REDUCER PRECIPITATION

(71) Applicant: Halliburton Energy Services, Inc., Houston, TX (US)

(72) Inventors: Leiming Li, Sugar Land, TX (US); Liang Xu, The Woodlands, TX (US); Scott Harris Bodnar, Houston, TX (US); Todd Allen Collier, Oklahoma City, OK (US); James William Ogle, Livingston, TX (US); Zhiwei Yue, Sugar Land, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 367 days.

(21) Appl. No.: 16/841,886

(22) Filed: Apr. 7, 2020

(65) Prior Publication Data
US 2021/0080439 A1    Mar. 18, 2021

Related U.S. Application Data (60) Provisional application No. 62/902,236, filed on Sep. 18, 2019.

(51) Int. Cl.
| | |
|---|---|
| *G01N 31/22* | (2006.01) |
| *C09K 8/80* | (2006.01) |
| *G01N 33/18* | (2006.01) |
| *C09K 8/66* | (2006.01) |

(52) U.S. Cl.
CPC .............. *G01N 31/22* (2013.01); *C09K 8/66* (2013.01); *C09K 8/80* (2013.01); *G01N 33/1813* (2013.01); *C09K 2208/28* (2013.01)

(58) Field of Classification Search
None
See application file for complete search history.

(56) References Cited

U.S. PATENT DOCUMENTS

| | | | | |
|---|---|---|---|---|
| 4,888,121 | A * | 12/1989 | Dill | ..................... C09K 8/528 507/261 |
| 8,188,012 | B2 | 5/2012 | Weerasooriya et al. | |
| 2003/0062316 | A1 * | 4/2003 | Mattox | ............... C09K 8/528 210/700 |
| 2009/0023613 | A1 | 1/2009 | Li et al. | |
| 2009/0023617 | A1 | 1/2009 | McMechan et al. | |
| 2009/0298721 | A1 | 12/2009 | Robb et al. | |
| 2013/0213657 | A1 | 8/2013 | Dobson, Jr. et al. | |

(Continued)

OTHER PUBLICATIONS

International Search Report and Written Opinion for Application No. PCT/US2020/028072, dated Jul. 31, 2020.

*Primary Examiner* — John J Figueroa
(74) *Attorney, Agent, or Firm* — Tenley Krueger; C. Tumey Law Group PLLC (57) ABSTRACT

A method may include: preparing or providing an aqueous fluid containing iron ions; screening at least one iron control agent against the aqueous fluid; selecting at least one iron control agent and iron control agent concentration based at least in part on the step of screening; and preparing a fracturing fluid comprising an aqueous base fluid and the at least one iron control agent wherein a concentration of the iron control agent in the fracturing fluid is greater than or equal to the selected iron control agent concentration.

18 Claims, 5 Drawing Sheets

(56) References Cited

U.S. PATENT DOCUMENTS

| | | | |
|---|---|---|---|
| 2013/0274155 A1* | 10/2013 | Nasr-El-Din | C09K 8/54 |
| | | | 507/241 |
| 2016/0075942 A1 | 3/2016 | Li et al. | |
| 2017/0327731 A1 | 11/2017 | Benoit et al. | |
| 2018/0016486 A1 | 1/2018 | German Borgogno | |
| 2019/0153303 A1 | 5/2019 | Riley et al. | |
| 2020/0048529 A1 | 2/2020 | Li et al. | |
| 2021/0079291 A1* | 3/2021 | Li | C09K 8/68 |

* cited by examiner

MITIGATION OF FRICTION REDUCER PRECIPITATION

CROSS REFERENCE TO RELATED APPLICATIONS

The present application claims priority to U.S. Provisional Application No. 62/902,236 filed Sep. 18, 2019, incorporated in its entirety be reference herein.

BACKGROUND

Hydrocarbon-producing wells may be stimulated by hydraulic fracturing operations, wherein proppants may be used to hold open or "prop" open fractures created during high-pressure pumping. Once the pumping-induced pressure is removed, proppants may prop open fractures in the rock formation and thus preclude the fracture from closing. As a result, the amount of formation surface area exposed to the well bore may be increased, enhancing hydrocarbon recovery rates.

An important component of hydraulic fracturing fluids is a friction reducer. Pumping rates for hydraulic fracturing operations may regularly exceed 50 barrels per minute (8 $m^3$/min) or more, which may cause turbulence in conduits such as wellbore tubing, liners, and casings. Turbulent flow of hydraulic fracturing fluids leads to high horsepower requirements to maintain pressure and flow rates. Some common friction reducers may include long chain water soluble polymers which may aid in moderating turbulence by reducing eddy currents within a conduit.

A friction reducer may be selected to be included in a fracturing fluid based at least in part on chemical properties of water available to mix the fracturing fluid at a well site. The properties of water such as dissolved species, pH, and temperature may affect the solubility of a friction reducer. A reduction in solubility may result in droplets of partially hydrated friction reducer to be present in the fracturing fluid. The droplets of partially hydrated friction reducer may result in less friction reduction as compared to a fluid which contains more hydrated friction reducer. Further, the drops of partially hydrated friction reducer may plug and foul surface and downhole equipment. Oftentimes water and solubility testing are performed prior to preparing a fracturing fluid to ensure the water source does not exhibit properties which may hinder the hydration of a friction reducer. When hydrolyzed friction reducing polymers contact with multivalent ions such as Fe ions, Ca ions, or Mg ions in formation brine, the solubility of the hydrolyzed friction reducing polymers may be reduced which may form insoluble precipitates. These precipitates may interfere with the functionality of stimulation equipment, effectively reversing at least some of the friction reducing capacity of the polymers and/or may cause damage to stimulation equipment. Additionally, these precipitates may intrude into the pores or openings within a formation resulting in damage to the formation or a reduction in formation conductivity.

BRIEF DESCRIPTION OF THE DRAWINGS

These drawings illustrate certain aspects of the present disclosure, and should not be used to limit or define the disclosure.

DETAILED DESCRIPTION

Figure 1:
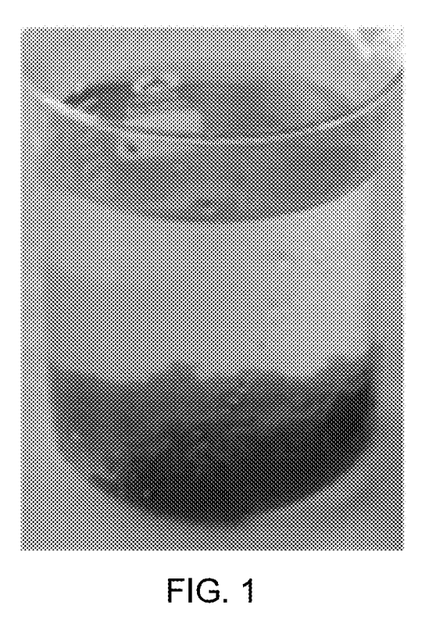
FIG. 1 is a photograph of an oilfield fluid sample containing precipitated friction reducer.

The present disclosure may relate to subterranean operations, and, in one or more implementations, to preventing dissolved multivalent cationic species from interfering with friction reducers such as anionic friction reducers. Friction reducers used in slickwater fracturing jobs may be acrylamide copolymer-based. Such friction reducers may be damaged by some dissolved multivalent cationic species such as iron ions in make up water and/or formation brine. The cationic species dissolved in the water may be electrically attracted to and associated with the anionic friction reducer which may result in a reduced solubility of the friction reducer leading to precipitates of friction reducer. These precipitates may reduce friction reduction efficiency and may cause stimulation equipment damage and formation damage. FIG. 1 shows an example of a fluid sample from oil field containing precipitated friction reducer or the so-called gummy bears recovered from a fracturing operation.

Formation of precipitated friction reducers may be driven by physicochemical properties of water including, but not limited to, concentration of soluble ions in water, chemical identity of friction reducer, and water pH, for example. The mitigation or reduction of precipitated friction reducers may be accomplished by various methods which will be described in greater detail herein, including, but not limited to, addition of control agents such as iron control agents, addition of pH control agent, addition of chelating agents, addition of flocculating agents, addition of oxygen scavenger, addition of surfactants, and addition of oxidative breaker species such as bromate, persulfate, and perbromate, for example.

There may be a wide variety of friction reducers available to be included in a fracturing fluid. Each friction reducer may have an operational range of where the friction reducer is able to hydrate and provide friction reduction. In examples where the water provided to mix the fracturing fluid has physicochemical properties outside of the operational range of the friction reducer, water treatment and/or chemical additives may be used to reduce or eliminate the precipitation of friction reducer. Friction reducing polymers may be polysaccharides or may be synthesized from a plurality of monomers, each of which may yield friction reducers with disparate properties. Additionally, manufacturing techniques and conditions may further influence the properties of a friction reducing polymer A screening method is therefore needed to determine if a friction reducer is susceptible to dissolved cationic species such as iron in water, and, if treatment may be needed to mitigate the effects of dissolved species on friction reducers.

By way of example, suitable friction reducing polymers may include any of a variety of monomeric units, such as acrylamide, acrylic acid, 2-acrylamido-2-methylpropane sulfonic acid, acrylamido tertiary butyl sulfonic acid, N,N-dimethylacrylamide, vinyl sulfonic acid, N-vinyl acetamide, N-vinyl formamide, itaconic acid, methacrylic acid, acrylic acid esters, methacrylic acid esters and combinations thereof. One example of a suitable anionic friction reducing polymer may include a polymer comprising acrylamide and acrylic acid and related salts or esters. The acrylamide and acrylic acid may be present in the polymer in any suitable concentration. An example of a suitable polymer may comprise acrylamide in an amount in the range of from about 5% to about 95% and acrylic acid in an amount in the range of from about 5% to about 95%. Another example of a suitable polymer may comprise acrylamide in an amount in the range of from about 60% to about 90% by weight and acrylic acid in an amount in the range of from about 10% to about 40% by weight. Another example of a suitable polymer may comprise acrylamide in an amount in the range of from about 80% to about 90% by weight and acrylic acid in an amount in the range of from about 10% to about 20% by weight. Yet another example of a suitable polymer may comprise acrylamide in an amount of about 85% by weight and acrylic acid in an amount of about 15% by weight. As previously mentioned, one or more additional monomers may be included in the polymer comprising acrylamide and acrylic acid. By way of example, the additional monomer(s) may be present in the friction reducing polymers in an amount up to about 20% by weight of the polymer. Suitable friction reducing polymers may be in an acid form or in a salt form. As will be appreciated, a variety of salts may be prepared, for example, by neutralizing the acid form of the acrylic acid monomer or the 2-acrylamido-2-methylpropane sulfonic acid monomer. In addition, the acid form of the polymer may be neutralized by ions present in the treatment fluid.

As discussed above, precipitates may can form when dissolved species such as iron ions in water (either make up water, formation water, or both) come into contact with friction reducing polymers. Although cations such as calcium ions, magnesium ions, barium ions may also associate with friction reducing polymers, iron ions usually have stronger bonding to the friction reducing polymers. In field locations, the iron concentration in make up water or formation brine may be low single digit parts per million. However, some water may have iron concentrations that may reach 20-80 ppm (parts per million), 200-400 ppm, or higher. By way of example, suitable iron control agent may include ethylenediaminetetraacetic acid (EDTA), N-(2-hydroxyethyl)ethylenediamine-N,N',N'-triacetic acid (HEDTA), glutamic acid, N,N-diacetic acid (GLDA), nitrilotriacetic acid (NTA), methylglycinediacetic acid (MGDA), their corresponding salts, and combinations thereof.

Water used in oilfield operations may be from various sources including surface water such as from lakes, rivers, estuaries, and oceans for example, as well as ground water from aquifers and water wells. One additional source of water in the oilfield may be produced water such as water that flows from a hydrocarbon well. Hydrocarbon wells often penetrate subterranean formations that contain a fraction of water alongside hydrocarbons. As such, fluids that are produced from a hydrocarbon well may contain hydrocarbons as well as a fraction of water. The produced fluids may be separated at the surface to generate a hydrocarbon stream and a water stream. The water stream may be further utilized to mix treatment fluids for well treatment such as drilling, cementing, stimulation, and enhanced recovery operations. The separated water stream may be referred to as produced water.

A downhole environment of a wellbore includes hydrocarbon-containing reservoirs which may contain various fluid phases including an aqueous fluid, hydrocarbon fluids, vapors, or gases—or any combination thereof. Pores in the reservoir are usually saturated by the aqueous fluid before migration of the hydrocarbon fluids. The aqueous fluid may be connate water, or groundwater that is trapped in the pores of a rock during formation of sedimentation. The aqueous fluid may also be formation water or interstitial water where water is found in the pores spaces of a rock and may not have been present during rock formation. Whether found in the pores or in the pore spaces, the aqueous fluid may be referred to as formation brine.

Formation of precipitated friction reducers may occur even in the downhole environment. The formation may be driven by physicochemical properties of the formation brine including, but not limited to, concentration of the soluble ions of the dissolved salts in the water, and water pH, for example. As previously discussed, cations such as iron ions may form precipitates with the friction reducing polymers. The iron concentration in the formation bring may be low single digit parts per million, while some water may have iron concentrations that may reach 20-80 ppm, 200-400 ppm, or higher. With areas of lower concentration of iron concentration, formation of precipitated friction reducers may occur slower, and gradually over a period of time. As the precipitated friction reducers continue to be deposited and accumulated in the wellbore, it may cause downhole equipment damage, as well as formation damage.

During preparation of treatment fluids, freshwater may be used as a base fluid with additional "make up" water used to make up the remaining volume of fluid required for a particular application. Make up water may be from any source as described above including surface water, ground water, and produced water, for example. Each of the sources of water may have varying levels of species dissolved therein, including those species previously described, which may affect the stability of friction reducers added to the water. While each of the previously mentioned source of water may be screened for dissolved species, another source of water that is not currently screened is formation brines. While formation brines are not typically directly added to a treatment fluid during preparation of the treatment fluid, once the treatment fluid is introduced into the formation, the treatment fluid and formation brines may contact and mix. Thus, if the water used to prepare a treatment fluid is screened for dissolved species and the water is deemed acceptable for a particular application, friction reducer precipitation may still occur when the treatment fluid is introduced into the subterranean formation and the dissolved species in the formation brine contact the friction reducer. As such, present screening methods employed in the oilfield may be inadequate to account for all sources of dissolved species.

A method of screening for compatibility of a friction reducer and water may include preparing a laboratory formation fluid, adding a friction reducing polymer to the laboratory formation fluid, and observing if precipitation of the friction reducing polymer occurs. The laboratory formation fluid may be prepared in a manner such that the concentration of dissolved species in the laboratory formation fluid may be representative of a treatment fluid after introduction of the treatment fluid into a subterranean formation. As discussed above, a volume of treatment fluid may be prepared and introduced into a subterranean formation whereby the treatment fluid may contact and mix with formation fluids such as a formation brine. The resulting fluid mixture of formation brine and treatment fluid may be referred to as a diluted treatment fluid and may be representative of a fluid that may be expected to be found in the subterranean formation after introducing the treatment fluid into the subterranean formation. While there may exist techniques to directly measure properties of the actual fluids present in a formation after the treatment fluid is introduced into the subterranean formation, it may be advantageous to model the diluted treatment fluid rather than performing the requisite well intervention techniques to directly sample the actual formation fluid.

Subterranean formations may contain varying volumes of formation brine. Some formations may contain a relatively large fraction of formation brine such that a volume of treatment fluid introduced therein may be diluted to a greater extent than a formation that contains a relatively smaller fraction of formation brine. Additionally, some formations may contain similar fractions of formation brine but may differ in concentration of dissolved species within the formation brine. In such examples, a diluted treatment fluid formed may have disparate concentrations of dissolved species depending on the concentration of dissolved species in formation brine. In general, the fluid content of a formation may be measured and/or estimated using open-hole or cased hole logging techniques as well as seismic logging techniques each of which may provide guidance to the fluid volume and dissolved species therein. Thus, a diluted treatment fluid model including the volume and concentration of dissolved species in the diluted formation fluid may be developed using the volume of formation brine and concentration of species therein and volume of treatment fluid and concentration of species therein. In some examples, a mixing model may be employed to further refine the diluted treatment fluid model such that a time dependent dissolved species concentration and/or a location dependent dissolved species concentration in the subterranean formation may be estimated. Thus, the diluted treatment fluid model may be used to predict a concentration of dissolved species in the diluted treatment fluid.

The above mentioned techniques for developing a diluted treatment fluid model may further be used to develop and prepare a laboratory formation fluid. The laboratory formation fluid may be prepared based at least in part on the diluted treatment fluid model. For example, the diluted treatment fluid model may indicate that a range of concentrations for a dissolved species may be expected to be present in a diluted treatment fluid. A laboratory formation fluid may be prepared with dissolved species in the ranges indicated by the model. Thereafter, a friction reducing polymer may be added to the laboratory treatment fluid and observed. In some examples, the laboratory treatment fluid containing the friction reducing polymer may be subjected to wellbore conditions such as wellbore pressure and temperature to simulate a wellbore. In some examples, the laboratory formation fluid may be prepared with dissolved species concentration in the range of 50% to about 500% of the diluted treatment fluid model. The laboratory formation fluid may be prepared with dissolved species concentration in the range of about 50% to about 100% of the diluted treatment fluid model, in the range of about 100% to about 200% of the diluted treatment fluid model, in the range of about 200% to about 300% of the diluted treatment fluid model, in the range of about 300% to about 400% of the diluted treatment fluid model, or in the range of about 400% to about 500% of the diluted treatment fluid model. There may be advantages to preparing a laboratory treatment fluid with a greater connection of dissolved species than a diluted treatment fluid model may predict. Relatively higher concentrations of dissolved species may react with a friction reducing polymer more quickly than relatively lower concentrations. For example, dissolved species may not immediately affect the stability and solubility of friction reducers when the friction reducers are added to a laboratory treatment fluid. The rate of reaction between the dissolved species and friction reducer may be increased by increasing the concentration of the dissolved species such that the precipitates, if present, may be observed within a reasonable timeframe of hours to days.

Utilizing the above described technique to estimate a concentration of dissolved species in the actual formation fluid may allow the behavior of a friction reducing polymer within a subterranean formation to be estimated. A simulated formation fluid may be prepared by providing water and increasing a concentration of cationic species therein until a desired concentration of dissolved cations is achieved. The dissolved cations ions may be any of those previously mentioned, including, but not limited to, iron ions, calcium ions, magnesium ions, aluminum ions, barium ions, and combinations thereof. The cations may be provided in any manner such as in a salt form, or may be generated in-situ by reaction, for example. The method may further include preparing a laboratory formation fluid and performing a screening test on a plurality of friction reducing polymers as described above. One or more friction reducing polymers may be selected based at least in part on the results of the screening test. A hydraulic fracturing fluid may then be prepared including the selected friction reducing polymer.

A hydraulic fracturing fluid may include an aqueous base fluid, a proppant, and a friction reducer. The aqueous based fluid may include fresh water, produced water, salt water, surface water, or any other suitable water. The term "salt water" is used herein to mean unsaturated salt solutions and saturated salt solutions including brines and seawater. The aqueous base fluid may include dissolved species of salts and metals that make up the total dissolved solids count for a particular sample of aqueous base fluid. Examples of dissolved species may include, but are not limited to, lithium, sodium, potassium, beryllium, magnesium, calcium, strontium, iron, zing, manganese, molybdenum, sulfur in the form of hydrogen sulfide, other sulfides, and sulfates, arsenic, barium, boron, chromium, selenium, uranium, fluorine, chlorine, bromine, iodine, and combinations thereof. One of ordinary skill in the art will understand that the present list of dissolved species is not exhaustive of all possible species dissolved in a particular sample of water. Furthermore, one of ordinary skill in the art will understand that particular dissolved species may be of concern with regards to performance of a particular fiction reducing polymer than other species. The water may be present in any amount by weight suitable for a particular hydraulic fracturing application. For example, without limitation, the water may be present at a point ranging from about 50 wt. % to about 100 wt. % based on a total weight of the hydraulic fracturing fluid. Alternatively, at a point ranging from about 50 wt. % to about 60 wt. %, at a point ranging from about 60 wt. % to about 70 wt. %, at a point ranging from about 70 wt. % to about 80 wt. %, at a point ranging from about 80 wt. % to about 90 wt. %, or at a point ranging from about 90 wt. % to about 100 wt. %. One of ordinary skill in the art with the benefit of this disclosure should be able to select an appropriate weight percent of water for a particular hydraulic fracturing fluid.

The hydraulic fracturing fluid may include a proppant. Proppants may include a collection of solid particles that may be pumped into the subterranean formation, such that the solid particles hold (or "prop") open the fractures generated during a hydraulic fracturing treatment. The proppant may include a variety of solid particles, including, but not limited to, sand, bauxite, ceramic materials, glass materials, polymer materials, polytetrafluoroethylene materials, nut shell pieces, cured resinous particulates including nut shell pieces, seed shell pieces, cured resinous particulates including seed shell pieces, fruit pit pieces, cured resinous particulates including fruit pit pieces, wood, composite particulates, and combinations thereof. Suitable composite particulates may include a binder and a filler material wherein suitable filler materials include silica, alumina, fumed carbon, carbon black, graphite, mica, titanium dioxide, meta-silicate, calcium silicate, kaolin, talc, zirconia, boron, fly ash, hollow glass microspheres, solid glass, and combinations thereof. The proppant may have any suitable particle size for a particular application such as, without limitation, nano particle size, micron particle size, or any combinations thereof. As used herein, the term particle size refers to a d50 particle size distribution, wherein the d50 particle size distribution is the value of the particle diameter at 50% in the cumulative distribution. The d50 particle size distribution may be measured by particle size analyzers such as those manufactured by Malvern Instruments, Worcestershire, United Kingdom. As used herein, nano-size is understood to mean any proppant with a d50 particle size distribution of less than 1 micron. For example, a proppant with a d50 particle size distribution at point ranging from about 10 nanometers to about 1 micron. Alternatively, a proppant with a d50 particle size distribution at point ranging from about 10 nanometers to about 100 nanometers, a proppant with a d50 particle size distribution at point ranging from about 100 nanometers to about 300 nanometers, a proppant with a d50 particle size distribution at point ranging from about 300 nanometers to about 700 nanometers, a proppant with a d50 particle size distribution at point ranging from about 700 nanometers to about 1 micron, or a proppant with a d50 particle size distribution between any of the previously recited ranges. As used herein, micron-size is understood to mean any proppant with a d50 particle size distribution at a point ranging from about 1 micron to about 1000 microns. Alternatively, a proppant with a d50 particle size distribution at point ranging from about 1 micron to about 100 microns, a proppant with a d50 particle size distribution at point ranging from about 100 microns to about 300 microns, a proppant with a d50 particle size distribution at point ranging from about 300 microns to about 700 micron, a proppant with a d50 particle size distribution at point ranging from about 700 microns to about 1000 microns, or a proppant with a d50 particle size distribution between any of the previously recited ranges.

Alternatively, proppant particle sizes may be expressed in U.S. mesh sizes such as, for example, 20/40 mesh (212 μm-420 μm). Proppants expressed in U.S. mesh sizes may include proppants with particle sizes at a point ranging from about 8 mesh to about 140 mesh (106 μm-2.36 mm). Alternatively a point ranging from about 16-30 mesh (600 μm-1180 μm), a point ranging from about 20-40 mesh (420 μm-840 μm), a point ranging from about 30-50 mesh (300 μm-600 μm), a point ranging from about 40-70 mesh (212 μm-420 μm), a point ranging from about 70-140 mesh (106 μm-212 μm), or alternatively any range there between. The standards and procedures for measuring a particle size or particle size distribution may be found in ISO 13503, or, alternatively in API RP 56, API RP 58, API RP 60, or any combinations thereof.

Proppants may include any suitable density. In some examples, proppants may have a density at a point ranging from about 1.25 g/cm$^3$ to about 10 g/cm$^3$. Proppants may include any shape, including but not limited, to spherical, toroidal, amorphous, planar, cubic, or cylindrical. Proppants may further include any roundness and sphericity. Proppant may be present in the fracturing fluid in any concentration or loading. Without limitation, the proppant may be present a point ranging from about 0.1 pounds per gallon ("lb/gal") (12 kg/m$^3$) to about 14 lb/gal (1677 kg/m$^3$). Alternatively, a point ranging from about 0.1 lb/gal (12 kg/m$^3$) to about 1 lb/gal (119.8 kg/m$^3$), a point ranging from about 1 lb/gal (119.8 kg/m$^3$) to about 3 lb/gal (359.4 kg/m$^3$), a point ranging from about 3 lb/gal (359.4 kg/m$^3$) to about 6 lb/gal (718.8 kg/m$^3$), a point ranging from about 6 lb/gal (718.8 kg/m$^3$) to about 9 lb/gal (1078.2 kg/m$^3$), a point ranging from about 9 lb/gal (1078.2 kg/m$^3$) to about 12 lb/gal (1437.6 kg/m$^3$), a point ranging from about 12 lb/gal (1437.6 kg/m$^3$) to about 14 lb/gal (1677.2 kg/m$^3$), or alternatively, any range therebetween.

Friction reducers may be included in the hydraulic fracturing fluid, for example, to form a slickwater fluid, for example. The friction reducer may be a polysaccharide or a synthetic polymer. Additionally, for example, the friction reducer may be an anionic polymer or a cationic polymer or a nonionic polymer. By way of example, suitable synthetic polymers may include any of a variety of monomeric units, including acrylamide, acrylic acid, 2-acrylamido-2-methylpropane sulfonic acid, acrylamido tertiary butyl sulfonic acid, N,N-dimethylacrylamide, vinyl sulfonic acid, N-vinyl acetamide, N-vinyl formamide, itaconic acid, methacrylic acid, acrylic acid esters, methacrylic acid esters and combinations thereof. Suitable friction reducers may be in an acid form or in a salt form. As will be appreciated by one of ordinary skill in the art, a variety of salts may be prepared, for example, by neutralizing the acid form of the acrylic acid monomer or the 2-acrylamido-2-methylpropane sulfonic acid monomer. In addition, the acid form of the polymer may be neutralized by ions present in the fracturing fluid. The term "polymer" in the context of a friction reducer, may be intended to refer to the acid form of the friction reducer, as well as its various salts.

The friction reducer may be included in the hydraulic fracturing fluid in the form of a liquid additive, for example, an amount ranging from about 0.1 gallons of the friction reducer per thousand gallons of the fracturing fluid ("GPT") to about 4 GPT or more. Alternatively, an amount ranging from about 0.1 GPT to about 0.5 GPT, an amount ranging from about 0.5 GPT to about 0.7 GPT, an amount ranging from about 0.7 GPT to about 1 GPT, an amount ranging from about 1 GPT to about 1.3 GPT, an amount ranging from about 1.3 GPT to about 1.6 GPT, an amount ranging from about 1.6 GPT to about 2 GPT, an amount ranging from about 2 GPT to about 2.5 GPT, an amount ranging from about 2.5 GPT to about 3 GPT, an amount ranging from about 3 GPT to about 3.5 GPT, an amount ranging from about 3.5 GPT to about 4 GPT, or alternatively, an amount ranging between any of the previously recited ranges. When provided as a liquid additive, the friction reducer may be in the form of an emulsion, a liquid concentrate, or both. One of ordinary skill will understand that a volume ratio such as GPT is equivalent to a volume ratio using a different basis such as liters or cubic meters. Additionally, the friction reducer may be provided as a dry additive and may be present in an amount ranging from about 0.01% wt. % to about 0.5 wt. % or more based on a total weight of the hydraulic fracturing fluid. Alternatively an amount ranging from about 0.01 wt. % to about 0.025 wt. %, an amount ranging from about 0.025 wt. % to about to about 0.04 wt. %, an amount ranging from about 0.04 wt. % to about 0.06 wt. %, an amount ranging from about 0.06 wt. % to about 0.09 wt. %, an amount ranging from about 0.09 wt. % to about 0.12 wt. %, an amount ranging from about 0.12 wt. % to about 0.15 wt. %, an amount ranging from about 0.15 wt. % to about 0.2 wt. %, an amount ranging from about 0.2 wt. % to about 0.25 wt. %, an amount ranging from about 0.25 wt. % to about 0.3 wt. %, an amount ranging from about 0.3 wt. % to about 0.35 wt. %, an amount ranging from about 0.35 wt. % to about 0.4 wt. %, an amount ranging from about 0.45 wt. % to about 0.5 wt. %, or alternatively, an amount ranging between any of the previously recited ranges.

Gelling agents may be included in the hydraulic fracturing fluid to increase the hydraulic fracturing fluid's viscosity which may be desired for some types of subterranean applications. For example, an increase in viscosity may be used for transferring hydraulic pressure to divert treatment fluids to another part of a formation or for preventing undesired leak-off of fluids into a formation from the buildup of filter cakes. The increased viscosity of the gelled or gelled and cross-linked treatment fluid, among other things, may reduce fluid loss and may allow the fracturing fluid to transport significant quantities of suspended proppant. Gelling agents may include, but are not limited to, any suitable hydratable polymer, including, but not limited to, galactomannan gums, cellulose derivatives, combinations thereof, derivatives thereof, and the like. Galactomannan gums are generally characterized as having a linear mannan backbone with various amounts of galactose units attached thereto. Examples of suitable galactomannan gums include, but are not limited to, gum arabic, gum ghatti, gum karaya, tamarind gum, tragacanth gum, guar gum, locust bean gum, combinations thereof, derivatives thereof, and the like. Other suitable gums include, but are not limited to, hydroxyethylguar, hydroxypropylguar, carboxymethylguar, carboxymethylhydroxyethylguar and carboxymethylhydroxypropylguar. Examples of suitable cellulose derivatives include hydroxyethyl cellulose, carboxyethylcellulose, carboxymethylcellulose, and carboxymethylhydroxyethylcellulose; derivatives thereof, and combinations thereof. The cross-linkable polymers included in the treatment fluids of the present disclosure may be naturally-occurring, synthetic, or a combination thereof. The crosslinkable polymers may include hydratable polymers that contain one or more functional groups such as hydroxyl, cis-hydroxyl, carboxyl, sulfate, sulfonate, phosphate, phosphonate, amino, or amide groups. In certain systems and/or methods, the crosslinkable polymers may be at least partially crosslinked, wherein at least a portion of the molecules of the crosslinkable polymers are crosslinked by a reaction including a crosslinking agent. The gelling agent may be present in the fracturing fluid in an amount ranging from about 0.5 lbs/1,000 gal of hydraulic fracturing fluid (0.05991 kg/m^3) to about 200 lbs/1,000 gal (23.946 kg/m^3). Alternatively, in an amount ranging from about 5 lbs/1,000 gal (0.5991 kg/m^3) to about 10 lbs/1,000 gal (1.198 kg/m^3), in an amount ranging from about 10 lbs/1,000 gal (1.198 kg/m^3) to about 15 lb/1,000 gal (1.797 kg/m^3), in an amount ranging from about 15 lb/1,000 gal (1.797 kg/m^3) to about 20 lb/1,000 gal (2.3946 kg/m^3), or alternatively, an amount ranging between any of the previously recited ranges.

The hydraulic fracturing fluid may include any number of additional optional additives, including, but not limited to, salts, acids, fluid loss control additives, gas, foamers, corrosion inhibitors, scale inhibitors, catalysts, clay control agents, biocides, friction reducers, iron control agent, antifoam agents, bridging agents, dispersants, hydrogen sulfide ("$H_2S$") scavengers, carbon dioxide ("$CO_2$") scavengers, oxygen scavengers, lubricants, viscosifiers, breakers, weighting agents, inert solids, emulsifiers, emulsion thinner, emulsion thickener, surfactants, lost circulation additives, pH control additive, buffers, crosslinkers, stabilizers, chelating agents, mutual solvent, oxidizers, reducers, consolidating agent, complexing agent, sequestration agent, control agent, particulate materials and any combination thereof. With the benefit of this disclosure, one of ordinary skill in the art should be able to recognize and select a suitable optional additive for use in the fracturing fluid.

Figure 2:
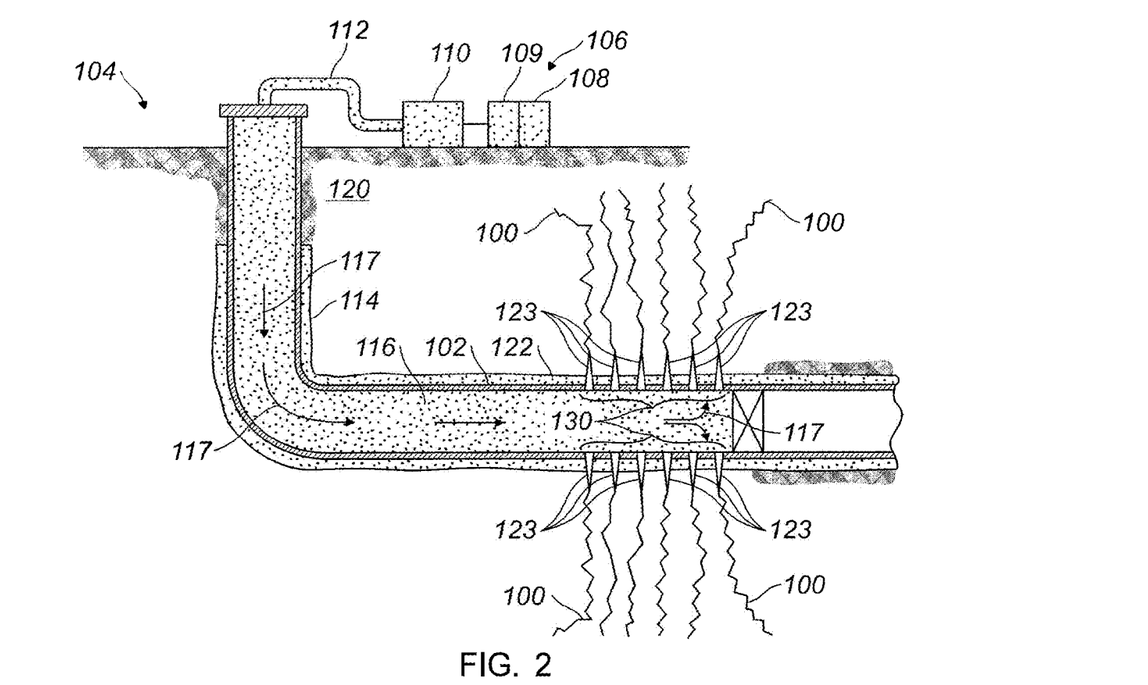
FIG. 2 is a schematic view of an example well system utilized for hydraulic fracturing.

FIG. 2 illustrates an example of a well system 104 that may be used to introduce proppant 116 into fractures 100. Well system 104 may include a fluid handling system 106, which may include fluid supply 108, mixing equipment 109, pumping equipment 110, and wellbore supply conduit 112. Pumping equipment 110 may be fluidly coupled with the fluid supply 108 and wellbore supply conduit 112 to communicate a fracturing fluid 117, which may include proppant 116 into wellbore 114. Proppant 116 may be any of the proppants described herein. The fluid supply 108 and pumping equipment 110 may be above the surface 118 while the wellbore 114 is below the surface 118.

Well system 104 may also be used for the pumping of a pad or pre-pad fluid into the subterranean formation at a pumping rate and pressure at or above the fracture gradient of the subterranean formation to create and maintain at least one fracture 100 in subterranean formation 120, The pad or pre-pad fluid may be substantially free of solid particles such as proppant, for example, less than 1 wt. % by weight of the pad or pre-pad fluid. Well system 104 may then pump the fracturing fluid 117 into subterranean formation 120 surrounding the wellbore 114. Generally, a wellbore 114 may include horizontal, vertical, slanted, curved, and other types of wellbore geometries and orientations, and the proppant 116 may generally be applied to subterranean formation 120 surrounding any portion of wellbore 114, including fractures 100. The wellbore 114 may include the casing 102 that may be cemented (or otherwise secured) to the wall of the wellbore 114 by cement sheath 122. Perforations 123 may allow communication between the wellbore 114 and the subterranean formation 120. As illustrated, perforations 123 may penetrate casing 102 and cement sheath 122 allowing communication between interior of casing 102 and fractures 100. A plug 124, which may be any type of plug for oilfield applications (e.g., bridge plug), may be disposed in wellbore 114 below the perforations 123.

In accordance with systems and/or methods of the present disclosure, a perforated interval of interest 130 (depth interval of wellbore 114 including perforations 123) may be isolated with plug 124. A pad or pre-pad fluid may be pumped into the subterranean formation 120 at a pumping rate and pressure at or above the fracture gradient to create and maintain at least one fracture 100 in subterranean formation 120. Then, proppant 116 may be mixed with an aqueous based fluid via mixing equipment 109, thereby forming a fracturing fluid 117, and then may be pumped via pumping equipment 110 from fluid supply 108 down the interior of casing 102 and into subterranean formation 120 at or above a fracture gradient of the subterranean formation 120. Pumping the fracturing fluid 117 at or above the fracture gradient of the subterranean formation 120 may create (or enhance) at least one fracture (e.g., fractures 100) extending from the perforations 123 into the subterranean formation 120. Alternatively, the fracturing fluid 117 may be pumped down production tubing, coiled tubing, or a combination of coiled tubing and annulus between the coiled tubing and the casing 102.

At least a portion of the fracturing fluid 117 may enter the fractures 100 of subterranean formation 120 surrounding wellbore 114 by way of perforations 123. Perforations 123 may extend from the interior of casing 102, through cement sheath 122, and into subterranean formation 120.

Figure 3:
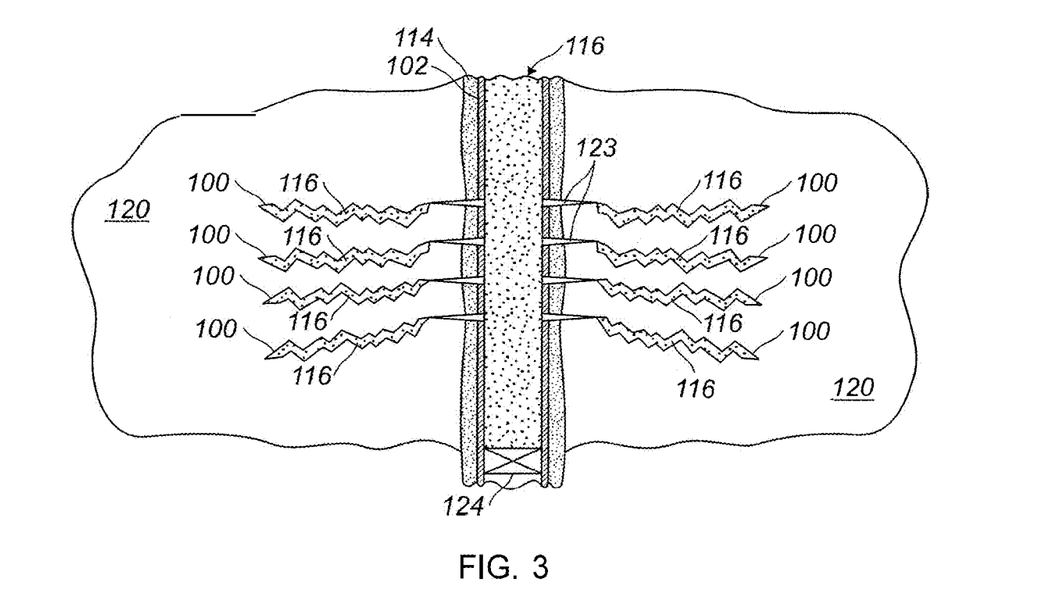
FIG. 3 is a schematic view of an example of a wellbore after introduction of fracturing fluid.

Referring to FIG. 3, the wellbore 114 is shown after placement of the proppant 116 in accordance with systems and/or methods of the present disclosure. Proppant 116 may be positioned within fractures 100, thereby propping open fractures 100.

The pumping equipment 110 may include a high pressure pump. As used herein, the term "high pressure pump" refers to a pump that is capable of delivering the fracturing fluid 117 and/or pad/pre-pad fluid downhole at a pressure of about 1000 psi (6894 kPa) or greater. A high pressure pump may be used when it is desired to introduce the fracturing fluid 117 and/or pad/pre-pad fluid into subterranean formation 120 at or above a fracture gradient of the subterranean formation 120, but it may also be used in cases where fracturing is not desired. Additionally, the high pressure pump may be capable of fluidly conveying particulate matter, such as the proppant 116, into the subterranean formation 120. Suitable high pressure pumps may include, but are not limited to, floating piston pumps and positive displacement pumps. Without limitation, the initial pumping rates of the pad fluid, pre-pad fluid and/or fracturing fluid 117 may range from about 15 barrels per minute ("bbl/min") (2385 l/min) to about 80 bbl/min (12719 l/min), enough to effectively create a fracture into the formation and place the proppant 116 into at least one fracture 101.

Alternatively, the pumping equipment 110 may include a low pressure pump. As used herein, the term "low pressure pump" refers to a pump that operates at a pressure of about 1000 psi (6894 kPa) or less. A low pressure pump may be fluidly coupled to a high pressure pump that may be fluidly coupled to a tubular (e.g., wellbore supply conduit 112). The low pressure pump may be configured to convey the fracturing fluid 117 and/or pad/pre-pad fluid to the high pressure pump. The low pressure pump may "step up" the pressure of the fracturing fluid 117 and/or pad/pre-pad fluid before it reaches the high pressure pump.

Mixing equipment 109 may include a mixing tank that is upstream of the pumping equipment 110 and in which the fracturing fluid 117 may be formulated. The pumping equipment 110 (e.g., a low pressure pump, a high pressure pump, or a combination thereof) may convey fracturing fluid 117 from the mixing equipment 109 or other source of the fracturing fluid 117 to the casing 102. Alternatively, the fracturing fluid 117 may be formulated offsite and transported to a worksite, in which case the fracturing fluid 117 may be introduced to the casing 102 via the pumping equipment 110 directly from its shipping container (e.g., a truck, a railcar, a barge, or the like) or from a transport pipeline. In either case, the fracturing fluid 117 may be drawn into the pumping equipment 110, elevated to an appropriate pressure, and then introduced into the casing 102 for delivery downhole.

A hydraulic fracturing operation may operate in stages where a bridge plug, frac plug, or other obstruction is inserted into the wellbore to prevent fluid communication with a region of the wellbore after the bridge plug. A perforating gun including explosive shaped charges may be inserted into a region of the wellbore before the bridge plug (i.e. a region where the measured depth is less than the measured depth of the bridge plug) and perforate holes through the walls of the wellbore. The perforating gun may be removed thereafter from the wellbore and a fracturing fluid introduced thereafter. The stage is completed when the planned volume of fluid and proppant has been introduced into the subterranean formation. Another stage may begin with the insertion of a second bridge plug into a wellbore region before the bridge plug.

The exemplary treatment fluids disclosed herein may directly or indirectly affect one or more components or pieces of equipment associated with the preparation, delivery, recapture, recycling, reuse, and/or disposal of the disclosed treatment fluids. For example, the disclosed treatment fluids may directly or indirectly affect one or more mixers, related mixing equipment, mud pits, storage facilities or units, composition separators, heat exchangers, sensors, gauges, pumps, compressors, and the like used generate, store, monitor, regulate, and/or recondition the exemplary treatment fluids. The disclosed treatment fluids may also directly or indirectly affect any transport or delivery equipment used to convey the treatment fluids to a well site or downhole such as, for example, any transport vessels, conduits, pipelines, trucks, tubulars, and/or pipes used to compositionally move the treatment fluids from one location to another, any pumps, compressors, or motors (e.g., topside or downhole) used to drive the treatment fluids into motion, any valves or related joints used to regulate the pressure or flow rate of the treatment fluids, and any sensors (i.e., pressure and temperature), gauges, and/or combinations thereof, and the like. The disclosed treatment fluids may also directly or indirectly affect the various downhole equipment and tools that may come into contact with the treatment fluids such as, but not limited to, wellbore casing, wellbore liner, completion string, insert strings, drill string, coiled tubing, slick line, wireline, drill pipe, drill collars, mud motors, downhole motors and/or pumps, cement pumps, surface-mounted motors and/or pumps, centralizers, turbolizers, scratchers, floats (e.g., shoes, collars, valves, etc.), logging tools and related telemetry equipment, actuators (e.g., electromechanical devices, hydro mechanical devices, etc.), sliding sleeves, production sleeves, plugs, screens, filters, flow control devices (e.g., inflow control devices, autonomous inflow control devices, outflow control devices, etc.), couplings (e.g., electro-hydraulic wet connect, dry connect, inductive coupler, etc.), control lines (e.g., electrical, fiber optic, hydraulic, etc.), surveillance lines, drill bits and reamers, sensors or distributed sensors, downhole heat exchangers, valves and corresponding actuation devices, tool seals, packers, cement plugs, bridge plugs, and other wellbore isolation devices, or components, and the like.

Accordingly, the present disclosure may provide methods relating to preparation of fracturing fluids and to a screening method for friction reducer precipitation. The methods may include any of the various features disclosed herein, including one or more of the following statements.

Statement 1. A method comprising: preparing or providing an aqueous fluid containing iron ions; screening at least one iron control agent against the aqueous fluid; selecting at least one iron control agent and iron control agent concentration based at least in part on the step of screening; and preparing a fracturing fluid comprising an aqueous base fluid and the at least one iron control agent wherein a concentration of the iron control agent in the fracturing fluid is greater than or equal to the selected iron control agent concentration.

Statement 2. The method of statement 1 wherein the step of preparing or providing comprises dissolving an iron containing compound in water or reacting an iron containing compound to release iron ions in water.

Statement 3. The method of any of statements 1-2 wherein the iron containing compound is $FeCl_2$.

Statement 4. The method of any of statements 1-3 wherein the aqueous fluid further comprises at least one ion selected from the group consisting of calcium ions, magnesium ions, sodium ions, barium ions, chloride ions, or combinations thereof.

Statement 5. The method of any of statements 1-4 wherein the iron control agent is selected from the group consisting of ethylenediaminetetraacetic acid (EDTA), N-(2-hydroxyethyl)ethylenediamine-N,N',N'-triacetic acid (HEDTA), glutamic acid, N,N-diacetic acid (GLDA), salts thereof, or combinations thereof.

Statement 6. The method of any of statements 1-5 wherein the aqueous base fluid is at least one of surface water, ground water, or produced water.

Statement 7. The method of any of statements 1-6 further comprising: screening a plurality of friction reducers against the aqueous fluid; selecting at least one friction reducer from the plurality of friction reducers based at least in part on the step of screening; and preparing the fracturing fluid including the at least one friction reducer.

Statement 8. The method of statement 7 wherein the plurality of friction reducers comprise at least one of a polyacrylamide, a polyacrylamide derivative, a synthetic polymer, an acrylamide copolymer, an anionic acrylamide copolymer, a cationic acrylamide copolymer, a nonionic acrylamide copolymer, an amphoteric acrylamide copolymer, a polyacrylate, a polyacrylate derivative, a polymethacrylate, a polymethacrylate derivative, polymers synthesized from one or more monomeric units selected from the group consisting of acrylamide, acrylic acid, 2-acrylamido-2-methylpropane sulfonic acid, acrylamido tertiary butyl sulfonic acid, N,N-dimethylacrylamide, vinyl sulfonic acid, N-vinyl acetamide, N-vinyl formamide, itaconic acid, methacrylic acid, acrylic acid esters, or methacrylic acid esters, their corresponding salts related salts, their corresponding esters, or combinations thereof.

Statement 9. The method of any of statements 1-8 wherein the fracturing fluid further comprises a proppant.

Statement 10. The method of any of statements 1-9 further comprising introducing the fracturing fluid into a subterranean formation.

Statement 11. A method of preparing a fracturing fluid comprising: preparing a laboratory treatment fluid based at least in part on a diluted treatment fluid model; screening at least one iron control agent against the laboratory treatment fluid; selecting at least one iron control agent and iron control agent concentration based at least in part on the step of screening; and preparing a fracturing fluid comprising an aqueous base fluid and the at least one iron control agent wherein a concentration of the iron control agent in the fracturing fluid is greater than or equal to the selected iron control agent concentration.

Statement 12. The method of statement 11 wherein the step of preparing a laboratory treatment fluid comprises dissolving an iron containing compound in water or reacting an iron containing compound to release iron ions in water such that a concentration of iron in the laboratory treatment fluid in the range of about 50% to about 500% of the diluted treatment fluid model.

Statement 13. The method of any of statements 11-12 wherein the diluted treatment fluid model includes a concentration of dissolved species in a diluted formation fluid, wherein the dissolved species comprises at least iron.

Statement 14. The method of any of statements 11-13 wherein the diluted treatment fluid model is based at least in part on measurement of a volume of formation brine and concentration of dissolved species therein and a volume of treatment fluid and concentration of dissolved species therein.

Statement 15. The method of any of statements 11-14 wherein the iron control agent is selected from the group consisting of ethylenediaminetetraacetic acid (EDTA), N-(2-hydroxyethyl)ethylenediamine-N,N',N'-triacetic acid (HEDTA), glutamic acid, N,N-diacetic acid (GLDA), salts thereof, or combinations thereof.

Statement 16. The method of any of statements 11-15 wherein the aqueous base fluid is at least one of surface water, ground water, or produced water.

Statement 17. The method any of statements 11-16 screening a plurality of friction reducers against the aqueous fluid; selecting at least one friction reducer from the plurality of friction reducers based at least in part on the step of screening; and preparing the fracturing fluid including the at least one friction reducer.

Statement 18. The method of any of statements 11-17 wherein the plurality of friction reducers comprise at least one of a polyacrylamide, a polyacrylamide derivative, a synthetic polymer, an acrylamide copolymer, an anionic acrylamide copolymer, a cationic acrylamide copolymer, a nonionic acrylamide copolymer, an amphoteric acrylamide copolymer, a polyacrylate, a polyacrylate derivative, a polymethacrylate, a polymethacrylate derivative, polymers synthesized from one or more monomeric units selected from the group consisting of acrylamide, acrylic acid, 2-acrylamido-2-methylpropane sulfonic acid, acrylamido tertiary butyl sulfonic acid, N,N-dimethylacrylamide, vinyl sulfonic acid, N-vinyl acetamide, N-vinyl formamide, itaconic acid, methacrylic acid, acrylic acid esters, or methacrylic acid esters, their corresponding salts related salts, their corresponding esters, or combinations thereof.

Statement 19. The method of any of statements 11-18 wherein the fracturing fluid further comprises a proppant.

Statement 20. The method of any of statements 11-19 further comprising introducing the fracturing fluid into a subterranean formation.

EXAMPLES

Figure 4:
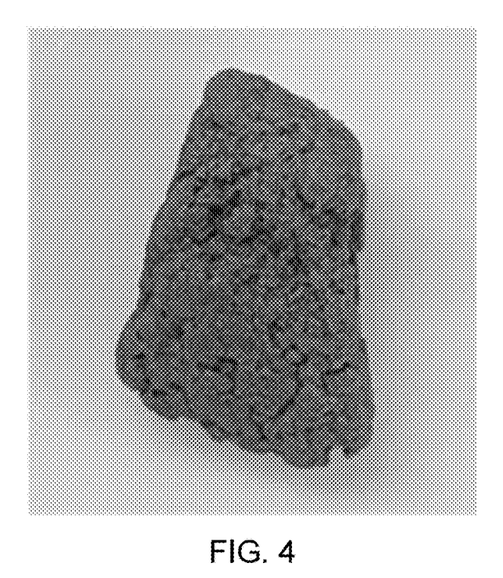
FIG. 4 is a photograph of a lab prepared friction reducer precipitate.

In one example, a friction reducer precipitate was prepared according the following method. 2000 ppm of $Fe^{2+}$ ions (in the form of $FeCl_2$ or its hydrate) was added to 500 ml of tap water, followed by the addition of 5 GPT of an anionic acrylamide copolymer-based friction reducer (emulsion, with about 40% by weight of dried acrylamide copolymer). It was observed that fluffy precipitates quickly formed when the iron ions and anionic acrylamide copolymer were mixed. The solution in the bottle was placed in 70° C. water bath. After one day, the solution in the bottle was taken out of the water bath. It was observed that precipitates had settled to the bottom of the solution. The solution was filtered with filter paper to produce filtered precipitate. The filtered precipitates were then dried to form the lab-prepared gummy bear illustrated in FIG. 4.

Figure 5:
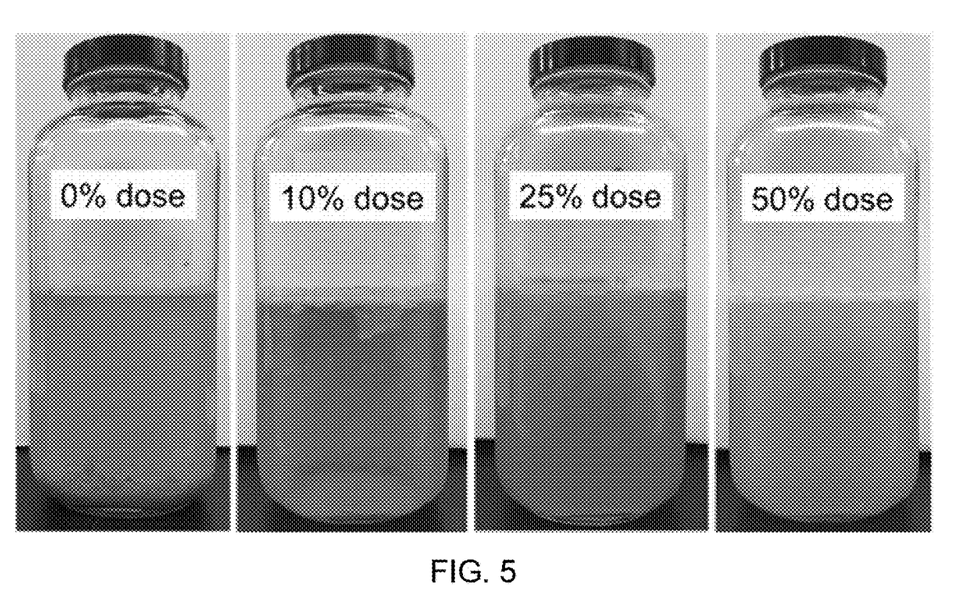
FIG. 5 is a photograph of four fluid samples containing anionic friction reducer and iron control agent.

Four fluid samples were prepared with tap water, 2000 ppm of $Fe^{2+}$ ions (in the form of $FeCl_2$ or its hydrate), and 5GPT of an anionic acrylamide copolymer-based friction reducer. Ethylenediaminetetraacetic acid (EDTA) salt was added to the fluid samples in an amount of 0%, 10%, 25%, and 50% molar ratios. The molar ratios indicates the molar ratio of EDTA to iron. 10% dose means that the molar ratio of the EDTA salt to the iron was 1:10 (or 10%). The samples were heated in 70° C. water bath for 1 day, and various degrees of precipitates were observed. The results of the tests with EDTA salt are shown in Table 1. A photograph of the samples with EDTA is shown in FIG. 5. In separate tests under the similar testing conditions, when 5 GPT of a cationic acrylamide copolymer-based friction reducer was added to the solution containing 2000 ppm of Fe2+ ions, the dried precipitate weight was 1.8 ppt, even without the addition of the EDTA salt. When 5 GPT of a nonionic acrylamide copolymer-based friction reducer was added to the solution containing 2000 ppm of Fe2+ ions, the dried precipitate weight was observed to be 3.8 ppt without the addition of the EDTA salt.

TABLE 1

Concentration of iron control agent vs. amount of dried precipitate.

| EDTA (molar ratio) | 0% | 10% | 25% | 50% |
|---|---|---|---|---|
| Dried Precipitates (ppt) | 19.5 | 5.7 | 2.5 | 2.5 |

Figure 6:
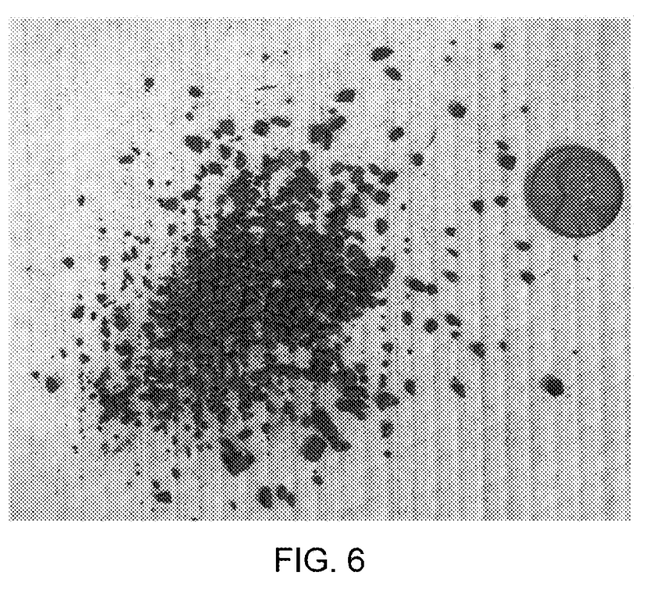
FIG. 6 is a photograph of shale cuttings.
Figure 7:
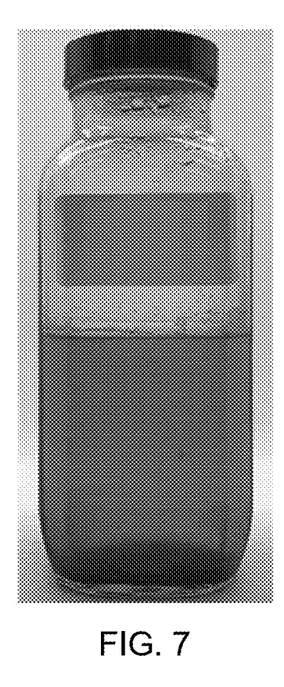
FIG. 7 is a photograph of a fluid sample containing anionic friction reducer, iron control agent, and shale cuttings.

In a second example, a field water sample was collected and 200 ppm of additional Fe2+ ions was added. 1 GPT of an anionic acrylamide copolymer-based friction reducer, 0.2 GPT scale inhibitor, 50% molar iron control agent, and 0.3 GPT biocide was added to the field water sample. A water analysis was performed before addition of the Fe2+ ions, the results of which are shown in Table 2. In addition, 1% by weight of shale cuttings from the field was also added to the sample. An X-Ray diffraction test was performed on the shale cuttings to characterize the mineral makeup of the shale cuttings. The results are shown in Table 3. A photograph of the shale cuttings is shown in FIG. 6. The solution was heated in a 70° C. water bath for 1 day. It was observed that barely any precipitates were seen in the bottle. FIG. 7 is a photograph of the shale cuttings after heating.

TABLE 2

Water analysis of field water sample.

| Species | PPM |
|---|---|
| Ca 2+ | 497 |
| Mg 2+ | 23 |
| Fe 2+ | 4 |
| Mn 2+ | 1 |
| Ba 2+ | 74 |
| Sr 2+ | 72 |
| Na+ | 2033 |
| K+ | 9 |
| Sulfate $SO_4^{2-}$ | 1 |
| Bicarbonate HCO3— | 124 |
| Cl— | 4168 |

TABLE 3

Mineral compositions of shale cuttings.

| Species | Wt. % |
|---|---|
| Quartz | 39 |
| Calcite | 12 |
| Dolomite | 5 |
| Albite | 20 |
| Pyrite | 2 |
| Smectite/Illite | 10 |
| Illite | 11 |
| Chlorite | 1 |

Figure 8:
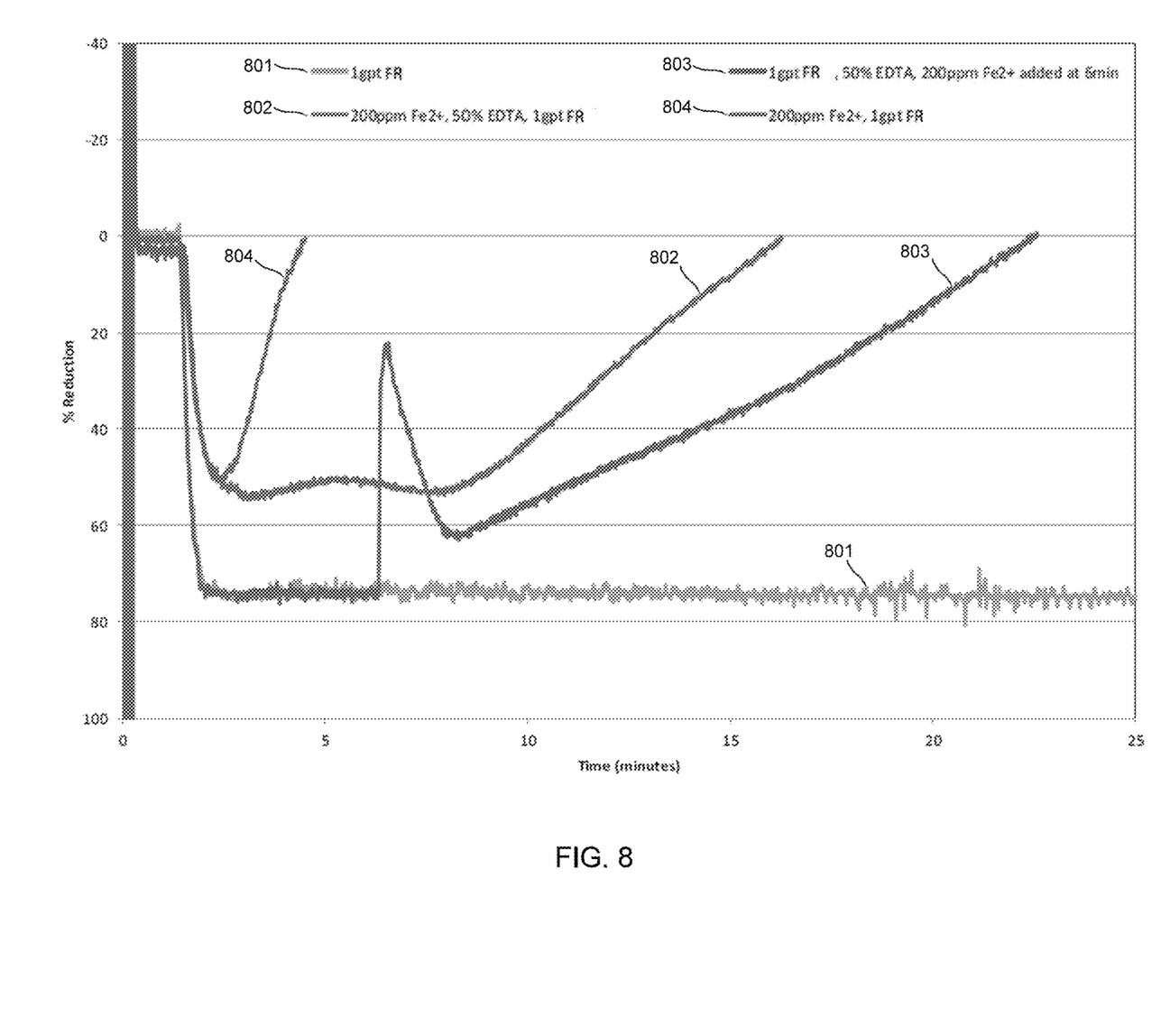
FIG. 8 is a graph of a flow loop test.

Friction loop tests were carried out to confirm if the iron control agent could mitigate the iron ion damage to an anionic friction reducing (FR) polymer. The friction flow loop used has an internal diameter of 0.5 inches and pressure sensors for monitoring throughout the duration of the test. Each flow loop run was done at ambient temperature and pressure, using 1 GPT of an anionic friction reducer in tap water with different iron and EDTA salt concentrations. All of the tests were done at a flow rate of 10 gallons per minute. FIG. 8 is a graphical depiction of friction loop tests. FIGS. 801, 802, 803, and 804 each provide a visualization of four conditions tested in the friction loop tests. A baseline test 801 with 1 GPT anionic friction reducer "FR" in tap water without iron ions showed the % friction reduction around 70% for the entire test duration of about 25 minutes. A second test 804, ("200 ppm Fe2+, 1 GPT FR") without the EDTA salt, 200 ppm Fe2+ in water quickly damaged the friction reduction capability of 1 GPT anionic friction reducer within about 5 minutes. In a third test 802, ("200 ppm Fe2+, 50% EDTA, 1 GPT FR"), 50% of the EDTA salt (molar ratio, relative to 200 ppm Fe2+) and 200 ppm Fe2+ were added to tap water first, and then 1 GPT anionic friction reducer was added, and then measured for about 15 minutes. The damage to the friction reduction was significantly mitigated compared with the case without the EDTA, or test 804. In a fourth test 803, ("1 GPT FR, 50% EDTA, 200 ppm Fe2+ added at 6 min"), 50% of the EDTA salt (molar ratio, relative to 200 ppm Fe2+) was added to water first, and 1 GPT anionic friction reducer was then added, and then measured for about 23 minutes. It was observed that the EDTA itself did not damage the % reduction of 70%. At ~6 minutes, 200 ppm Fe2+ was added. Again, the damage to the friction reduction was significantly mitigated compared with the case without the EDTA. This test simulated the case where slickwater with the iron control agent was pumped downhole and later mixed the high-iron formation brine there.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present embodiments are well adapted to attain the ends and advantages mentioned as well as those that are inherent therein. The particular embodiments disclosed above are illustrative only, as the present embodiments may be modified and practiced in different but equivalent manners apparent to those skilled in the art having the benefit of the teachings herein. Although individual embodiments are discussed, all combinations of each embodiment are contemplated and covered by the disclosure. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of the present disclosure. If there is any conflict in the usages of a word or term in this specification and one or more patent(s) or other documents that may be incorporated herein by reference, the definitions that are consistent with this specification should be adopted.

What is claimed is:

1. A method comprising:
preparing or providing an aqueous fluid containing iron ions;
screening at least one iron control agent against the aqueous fluid;
selecting at least one iron control agent and iron control agent concentration based at least in part on the step of screening;
screening a plurality of friction reducers against the aqueous fluid;
selecting at least one friction reducer from the plurality of friction reducers based at least in part on the step of screening;
preparing a fracturing fluid comprising an aqueous base fluid, the at least one friction reducer, and the at least one iron control agent wherein a concentration of the iron control agent in the fracturing fluid is greater than or equal to the selected iron control agent concentration.

2. The method of claim 1 wherein the step of preparing or providing comprises dissolving an iron containing compound in water or reacting an iron containing compound to release iron ions in water.

3. The method of claim 2 wherein the iron containing compound is $FeCl_2$.

4. The method of claim 1 wherein the aqueous fluid further comprises at least one ion selected from the group consisting of calcium ions, magnesium ions, sodium ions, barium ions, chloride ions, or combinations thereof.

5. The method of claim 1 wherein the iron control agent is selected from the group consisting of ethylenediaminetetraacetic acid (EDTA), N-(2-hydroxyethyl)ethylenediamine-N,N',N'-triacetic acid (HEDTA), glutamic acid, N,N-diacetic acid (GLDA), salts thereof, or combinations thereof.

6. The method of claim 1 wherein the aqueous base fluid is at least one of surface water, ground water, or produced water.

7. The method of claim 1 wherein the plurality of friction reducers comprise at least one of a polyacrylamide, a polyacrylamide derivative, a synthetic polymer, an acrylamide copolymer, an anionic acrylamide copolymer, a cationic acrylamide copolymer, a nonionic acrylamide copolymer, an amphoteric acrylamide copolymer, a polyacrylate, a polyacrylate derivative, a polymethacrylate, a polymethacrylate derivative, polymers synthesized from one or more monomeric units selected from the group consisting of acrylamide, acrylic acid, 2-acrylamido-2-methylpropane sulfonic acid, acrylamido tertiary butyl sulfonic acid, N,N-dimethylacrylamide, vinyl sulfonic acid, N-vinyl acetamide, N-vinyl formamide, itaconic acid, methacrylic acid, acrylic acid esters, or methacrylic acid esters, their corresponding salts related salts, their corresponding esters, or combinations thereof.

8. The method of claim 1 wherein the fracturing fluid further comprises a proppant.

9. The method of claim 1 further comprising introducing the fracturing fluid into a subterranean formation.

10. A method of preparing a fracturing fluid comprising:
preparing a laboratory treatment fluid based at least in part on a diluted treatment fluid model;
screening at least one iron control agent against the laboratory treatment fluid;
selecting at least one iron control agent and iron control agent concentration based at least in part on the step of screening;
screening a plurality of friction reducers against the aqueous fluid;
selecting at least one friction reducer from the plurality of friction reducers based at least in part on the step of screening; and
preparing a fracturing fluid comprising an aqueous base fluid, the at least one friction reducer, and the at least one iron control agent wherein a concentration of the iron control agent in the fracturing fluid is greater than or equal to the selected iron control agent concentration.

11. The method of claim 10 wherein the step of preparing a laboratory treatment fluid comprises dissolving an iron containing compound in water or reacting an iron containing compound to release iron ions in water such that a concentration of iron in the laboratory treatment fluid in the range of about 50% to about 500% of the diluted treatment fluid model.

12. The method of claim 10 wherein the diluted treatment fluid model includes a concentration of dissolved species in a diluted formation fluid, wherein the dissolved species comprises at least iron.

13. The method of claim 10 wherein the diluted treatment fluid model is based at least in part on measurement of a volume of formation brine and concentration of dissolved species therein and a volume of treatment fluid and concentration of dissolved species therein.

14. The method of claim 10 wherein the iron control agent is selected from the group consisting of ethylenediaminetetraacetic acid (EDTA), N-(2-hydroxyethyl)ethylenediamine-N,N',N'-triacetic acid (HEDTA), glutamic acid, N,N-diacetic acid (GLDA), salts thereof, or combinations thereof.

15. The method of claim 10 wherein the aqueous base fluid is at least one of surface water, ground water, or produced water.

16. The method of claim 10 wherein the plurality of friction reducers comprise at least one of a polyacrylamide, a polyacrylamide derivative, a synthetic polymer, an acrylamide copolymer, an anionic acrylamide copolymer, a cationic acrylamide copolymer, a nonionic acrylamide copolymer, an amphoteric acrylamide copolymer, a polyacrylate, a polyacrylate derivative, a polymethacrylate, a polymethacrylate derivative, polymers synthesized from one or more monomeric units selected from the group consisting of acrylamide, acrylic acid, 2-acrylamido-2-methylpropane sulfonic acid, acrylamido tertiary butyl sulfonic acid, N,N-dimethylacrylamide, vinyl sulfonic acid, N-vinyl acetamide, N-vinyl formamide, itaconic acid, methacrylic acid, acrylic acid esters, or methacrylic acid esters, their corresponding salts related salts, their corresponding esters, or combinations thereof.

17. The method of claim 10 wherein the fracturing fluid further comprises a proppant.

18. The method of claim 10 further comprising introducing the fracturing fluid into a subterranean formation.

* * * * *